US011285254B2

(12) United States Patent
Lu et al.

(10) Patent No.: US 11,285,254 B2
(45) Date of Patent: Mar. 29, 2022

(54) EXTRACORPOREAL LIFE SUPPORT SYSTEM

(71) Applicants: 3R LIFE SCIENCES TAIWAN LTD., Kaohsiung (TW); Hsiao-Chien Lin, Grand Cayman (KY)

(72) Inventors: Pong-Jeu Lu, Grand Cayman (KY); Hsiao-Chien Lin, Grand Cayman (KY)

(73) Assignee: 3R Life Sciences Ltd., Kaohsiung (TW)

(*) Notice: Subject to any disclaimer, the term of this patent is extended or adjusted under 35 U.S.C. 154(b) by 614 days.

(21) Appl. No.: 16/317,083

(22) PCT Filed: Jul. 12, 2017

(86) PCT No.: PCT/US2017/041653
§ 371 (c)(1),
(2) Date: Jan. 11, 2019

(87) PCT Pub. No.: WO2018/013644
PCT Pub. Date: Jan. 18, 2018

(65) Prior Publication Data
US 2019/0247564 A1 Aug. 15, 2019

Related U.S. Application Data

(60) Provisional application No. 62/361,050, filed on Jul. 12, 2016.

(51) Int. Cl.
*A61M 1/36* (2006.01)
*A61M 1/16* (2006.01)

(52) U.S. Cl.
CPC ........ *A61M 1/3667* (2014.02); *A61M 1/1698* (2013.01); *A61M 1/3607* (2014.02); *A61M 1/3624* (2013.01); *A61M 2230/04* (2013.01)

(58) Field of Classification Search
CPC . A61M 1/3667; A61M 1/1698; A61M 1/3659
See application file for complete search history.

(56) References Cited

U.S. PATENT DOCUMENTS 5,916,193 A * 6/1999 Stevens ................ A61F 2/2433
604/509

* cited by examiner

*Primary Examiner* — Leslie R Deak
(74) *Attorney, Agent, or Firm* — Rosenberg, Klein & Lee

(57) ABSTRACT

The present invention provides a method, system, and apparatus that can substantially reduce the recirculation of venovenous extracorporeal membrane oxygenation (VV ECMO) associated with the two-site, single-lumen cannulation approach. Actively-controlled flow regulators comprising balloon, occluder and reservoir can be individually or collectively equipped on the drainage and/or infusion cannulas to accomplish the goal of maximizing VV ECMO support efficacy. Three specific embodiments are introduced to illustrate the practical enforcement of the proposed blood flow control in reference to the heart rhythm, aiming at achieving the maximal reduction of oxygenated blood flow recirculating back to the VV ECMO circuit.

5 Claims, 17 Drawing Sheets

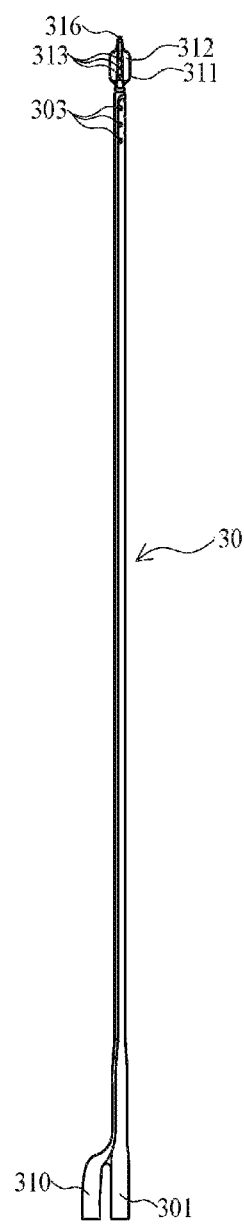
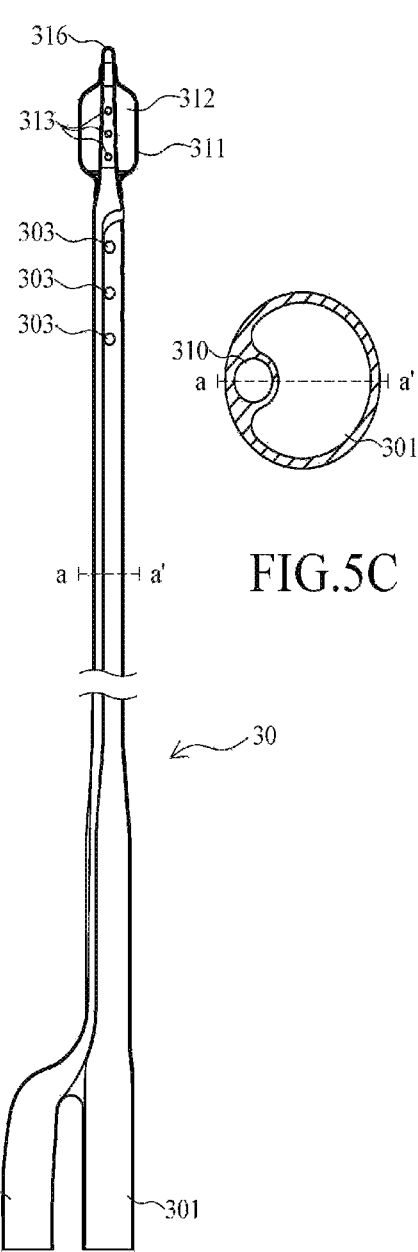
FIG.5C
FIG.5A  FIG.5B

EXTRACORPOREAL LIFE SUPPORT SYSTEM

REFERENCE TO RELATED APPLICATIONS

This application is based on Provisional application Ser. No. 62/361,050, filed Jul. 12, 2016, currently pending.

FIELD OF THE INVENTION

The present invention relates to an extracorporeal life support system, and more particular an actively-controlled flow regulator method associated with a veno-venous extracorporeal membrane oxygenation (VV ECMO) system, intended to prevent the oxygenated blood flow from circulating back to the ECMO circuit via the drainage cannula. More specifically, the invention intends to further improve the recirculation phenomena by an actively-controlled regulator system that can impede or accelerate the cannula flows using electrocardiogram (ECG) as timing reference, aiming at maximizing oxygenated blood convected into right ventricle during heart diastole when tricuspid valve is open; whereas reducing oxygenated blood flow infused into, while maximizing deoxygenated venous return to, the right atrium/vena cava during heart systole when tricuspid valve is closed.

BACKGROUND OF THE INVENTION

Worldwide use of extracorporeal membrane oxygenation (ECMO) system for salvaging severe respiratory diseases such as Acute Respiratory Distress Syndrome (ARDS) escalates since the bird flu pandemic in 1992. At present, approximately 40% of annual ECMO usage has been associated with the treatment of ARDS or other advanced respiratory diseases, in which cannulation method and design is crucial for an effective pulmonary disease treatment.

ECMO is conventionally divided into two categories of veno-arterial (VA) ECMO and veno-venous (VV) ECMO configurations. VA ECMO is intended for treating heart failure patients while VV ECMO for respiratory failure patients. The pulmonary extracorporeal circuit of VV ECMO originated from a two-site, single-lumen cannula insertion method, with drainage and infusion cannula disposed respectively in inferior vena cava (IVC) and superior vena cava (SVC). This most commonly seen VV ECMO has its drainage cannula inserted from groin and advanced through the IVC, while placing its infusion cannula from jugular vein and advanced through SVC, until both cannulas meet in the right atrium (RA) region. Owing to the closely placed drainage and infusion cannula tips, a significant portion of infused oxygenated blood might be sucked into the drainage cannula instead of entering the RA, creating a phenomenon termed "Recirculation" that jeopardizes the support efficacy of VV ECMO. In general, recirculation rate increases as the ECMO flow increases despite that larger ECMO flow is required for by the more severely damaged lungs. As recirculation prevails, not only support efficacy of VV ECMO is compromised, but also complications resulting from extra blood cell damage caused by longer residence time in the ECMO circuit are highly undesirable. For example, blood cells will be lysed more when recirculating longer in the ECMO circuit, in particular in the narrow fiber channels of the oxygenator, leading to bleeding or thromboembolic complications secondary to heavier dosage of heparin anti-coagulation that is required.

There have been solutions proposed for mitigating recirculation of VV ECMO. Practical enforcement focused on improving the cannula design and the associated cannulation method. There are four types of cannula/cannulation in VV ECMO: 1) two-site, single-lumen cannulation, 2) one-site, double-lumen cannulation, 3) two-site, double-lumen cannulation, and 4) three-site, single-lumen cannulation. In recent years, one-site, double-lumen cannulation realized by Avalon cannula gains popularity due to its advantages of improved recirculation reduction and being able to offer patients better mobile capability for quicker lung recovery.

All the above-mentioned cannulation methods adopt passive design concept involving no actively regulated actuators in the minimization of recirculation. It is worth noticing that right ventricle (RV) only accepts infused oxygenated blood during heart diastole when tricuspid valve opens. During heart systole, the tricuspid valve is closed so the infused oxygenated blood cannot go into RV no matter how the infusion cannula tip is placed in close proximity to the tricuspid valve entrance. This is the basic root cause that limits the performance ceiling of all passive cannulation options. Assessment of VV ECMO recirculation has been conducted on a specially designed pulmonary mock circulation loop in the inventor's laboratory. At the ECMO flow of 3.5 Liter/min, the recirculation rate of conventional two-site, single-lumen cannulation is high in the 40-50% range, and one-site, double-lumen Avalon cannulation is around 20-25%. There still exists ample room for further improvement that can be made to benefit patients requiring pulmonary ECMO treatment.

Patients on ECMO are often sedated and bedridden in the Intensive Care Unit (ICU). The advantage associated with one-site, double-lumen cannula for ambulating patient to expedite recovery period is, in practice, difficult to realize. As a matter of fact, in vast majority ICUs worldwide, the nurse and staff support in ICU is inadequate to allow ECMO patients leaving bed and safely walking around the corridors in ICU in a routine manner.

The size of an ECMO cannula is in general restricted because excessively large cannula is difficult to insert and may cause intra-operative vessel lesion and narrowed vascular lumen after cannula removal. The infusion and drainage flow passages co-existing in a double-lumen cannula are inherently smaller than that of a single-lumen cannula. Higher flow resistance/wall shear stress pertaining to one-site, double-lumen cannulation inevitably results in more blood cell damage as blood stream is first drained and then re-infused through the narrower passages of the double-lumen cannula. In fact, ECMO flow in double-lumen cannulation has been significantly limited by its high flow resistance, which is non-ideal for supporting advanced respiratory failure patients who urgently need larger ECMO flow.

SUMMARY OF THE INVENTION

The present invention adopts a two-site, double-lumen cannulation approach that is specially designed to further reducing recirculation by employing an ECG-gated anti-recirculation controller system, as shown subsequently. Notice that, unlike the lumen categorization defined previously, in the present invention, double-lumen is defined as a tubular integration consisting of an air passage and a blood passage, of which the cross-section of the blood passage is much wider than that of the air passage. Literally speaking, the blood flow resistance of the present double-lumen cannula is comparable to that of the aforementioned single-lumen cannula. Full advantage in hemodynamics is hence taken in terms of larger support flow with smaller flow resistance. With the adoption of larger blood flow passages in cannula, the much reduced tubular flow shear stress will lead to fewer blood cell damage requiring lesser heparin and anti-platelet administration.

By regulating drainage/infusion flow speed profiles in accord to tricuspid valve opening/closure state, VV ECMO recirculation can thus be minimized to an unprecedented rate that the existing prior arts cannot achieve. In the inventor's opinion, further cutting down the state-of-the-art recirculation rate while widening ECMO flow support range under lower blood cell damage presumption is a more desirable treatment option than that offered by the current one-site, double-lumen cannulation. When VV ECMO support efficacy is further improved via actively-controlled actuators mounted on the cannulas, taking into account both time elapse and blood flow characteristics associated with tricuspid valvular motion, the diseased lung can hitherto rest more adequately leading to a faster recovery, and the time period spent on ECMO and in ICU will be substantially reduced to truly benefit the patients. Rehabilitation that helps patient's lung to recover sooner can be conducted after patients are weaned from ECMO and moved out of ICU.

The present invention involves a novel blood flow regulator system designed for enhancing the effectiveness of Venovenous Extracorporeal Membrane Oxygenation (VV ECMO). This actively-controlled ECMO system comprises a drainage cannula, an infusion cannula, a blood pump, an oxygenator, and an electrocardiogram (ECG)-gated controller and a pneumatic driver. The present drainage cannula assembly, which draws deoxygenated blood from vena cava into the ECMO system, comprises a drainage cannula, a compliant reservoir, a drainage site occluder, and a first balloon. The cannula assembly for the ECMO return site, which infuses ECMO-oxygenated blood back into vena cava or right atrium (RA), comprises an infusion cannula, a compliant reservoir, a return site occluder, and a second balloon. Those actively or passively driven parts, namely the balloon, the occluder and the reservoir, which can be adopted in full or in part in the controller system design, constitute the present cannula flow regulating elements that are actuated by a commanding control logic using ECG signal as the triggering reference. Intermittent occluder-controlled venous return and ECMO-powered flow drainage and reentry, coordinated in response to the tricuspid valve opening and closure, will achieve a maximized oxygenated blood flow that primes the right ventricle (RV) and subsequently be ejected into the pulmonary circulation. By using this ECG-gated VV ECMO invention, the recirculation of oxygenated blood back into the ECMO circuit can significantly be reduced, resulting in the desired alleviation of the respiratory demand imposed on the diseased lungs. Moreover, the reduction of blood recirculation phenomenon will shorten the residence time of blood cells circulating in the ECMO circuit, contributing to lesser blood cell damage such as hemolysis, thromboembotic events, and neurological stroke risks.

The drainage or infusion cannula of the present invention comprises an inflatable balloon that may wrap a portion of the cannula outer surface or is supported by a catheter that physically situated close to and functions together with the said cannula. Balloon material should be durable and biocompatible, and is made of, for example, deformable or distensible elastomer. When deflated, this balloon is shrunk into low profile so as to minimize the flow resistance. When inflated, the balloon is expanded against or in close proximity to the vascular wall so as to obstruct the blood flow passage. This intra-vascular cannula-balloon assembly is placed within the large vein and responsible for blood drainage and/or reentry. By controlling the inflation and deflation of the balloon on the cannula, the obstruction interval for and the volume of venous return coming out of the superior vena cava (SVC) or the inferior vena cava (IVC) to the right atrium are regulated.

Each cannula of the present invention may further be provided with an adjustable occluder mounted on the cannula and located outside of the patient's body. Occluder is a mechanism meant for compressing down the cross-sectional area of the controlled tubular flow and hence reducing the flow rate. In other words, it impedes the internal tubular flow by increasing the flow resistance. Alternatively, internal flow impedance contributed by interior balloon or flexing membrane can be taken as a generalized occluder. By pinching the occluder with different occlusion degree, squeezing timing, and time interval, the blood flow passage in the cannula lumen can be regulated to be open, partially open or closed in the time series. The time interval for and the volume of the venous return withdrawn into the ECMO inflow end as well as the oxygenated blood issued out of the ECMO outflow end can thus be regulated.

The ECMO inflow and outflow paths are fluid communicated with reservoirs as a capacitance mechanism for storing and/or returning blood in conjunction with the ECMO circuit flow, which is required for facilitating a steady and continuous blood pump operation when balloon or occluder is in action in the loop. Passive reservoirs can be built using elastic materials, which functions in a manner similar to that of a compliant human vessel. Active reservoir can also be built like a displacement pump with pump volume controlled by an external driver system. Reservoir can be placed either in series or in parallel to the flow passage. In-line type reservoir is preferred for a simpler design and a more streamlined flow passage. However, in certain situation, actively-controlled fluid volume primed into or extracted out of the reservoir may be instrumental to help regulate the ECMO circuit flow.

Both balloons and occluders are activated using ECG signal as the triggering reference signal. The control of inflation/deflation of the balloons and the opening/closure of the occluders can be set individually or in a combinatory group, timed properly in relation to the opening and closure timings of the tricuspid valve. The aim is to maximize the oxygenated blood volume stored in the RA before tricuspid valve opens (preparing for subsequent filling of the RV during diastole) whereas withdrawing maximal oxygen-depleted venous return into the ECMO circuit when the tricuspid valve is closed during heart systole. In addition, reservoirs are functioning together with the occluders, in the sense that the impeded ECMO flow during occluder closure will be compensated in the next phase when occluder opens and the reservoir works like a booster to expel the pressurized, stored blood volume back into the ECMO flow. With the use of the present ECG-gated VV ECMO invention, the conventional drawback of recirculating oxygenated blood back into the ECMO circuit can be substantially reduced without penalty paid in ECMO flow reduction.

BRIEF DESCRIPTIONS OF THE DRAWINGS

A more particular description of the invention briefly stated may be realized by the embodiments thereof illustrated in the appended drawings. Understanding that these drawings depict only typical embodiments of the invention, which is not to be considered limiting of its scope. The presently referred embodiments and the best mode of the invention will be described using the accompanying drawings in which.

Figure 3A:
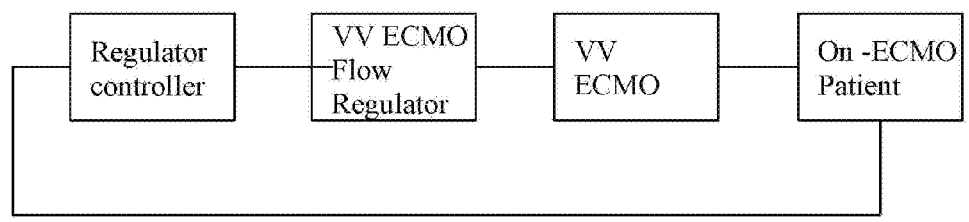
FIG. 3A is the control block diagram of the present invention.
Figure 3B:
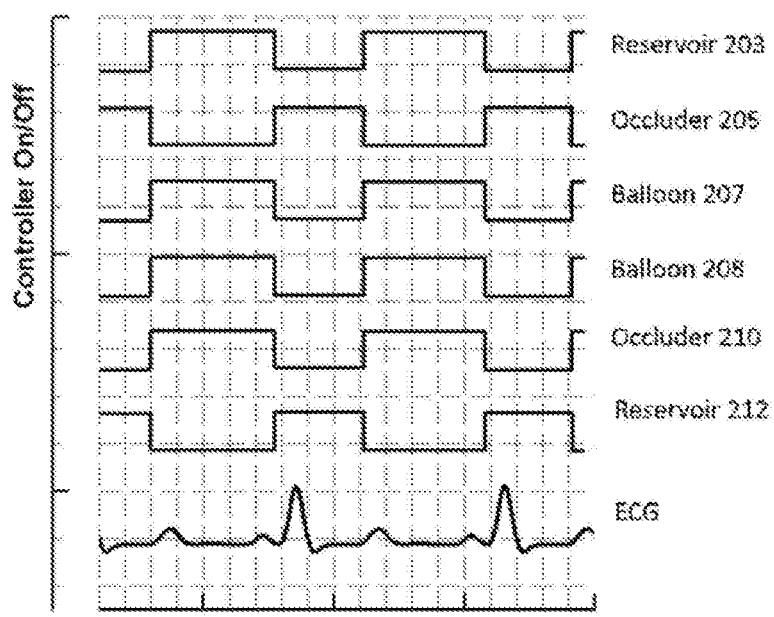

FIG. 3B schematically depicts the triggering timing (control-on or control-off) associated with each flow regulator.

Figure 4A:
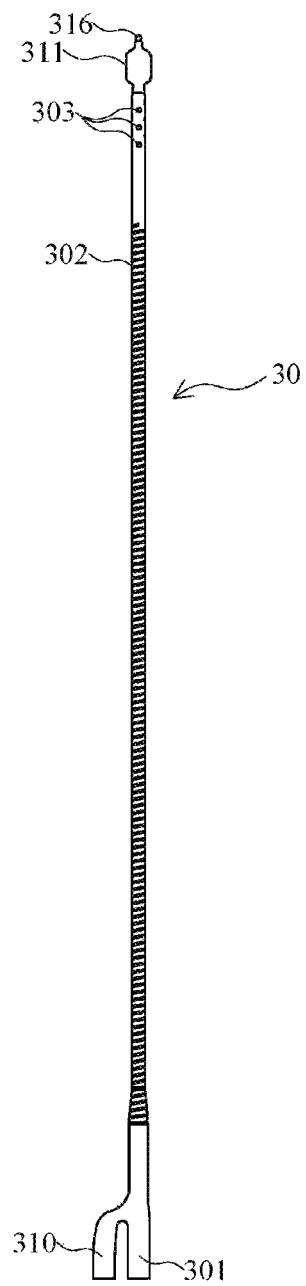
Figure 4B:
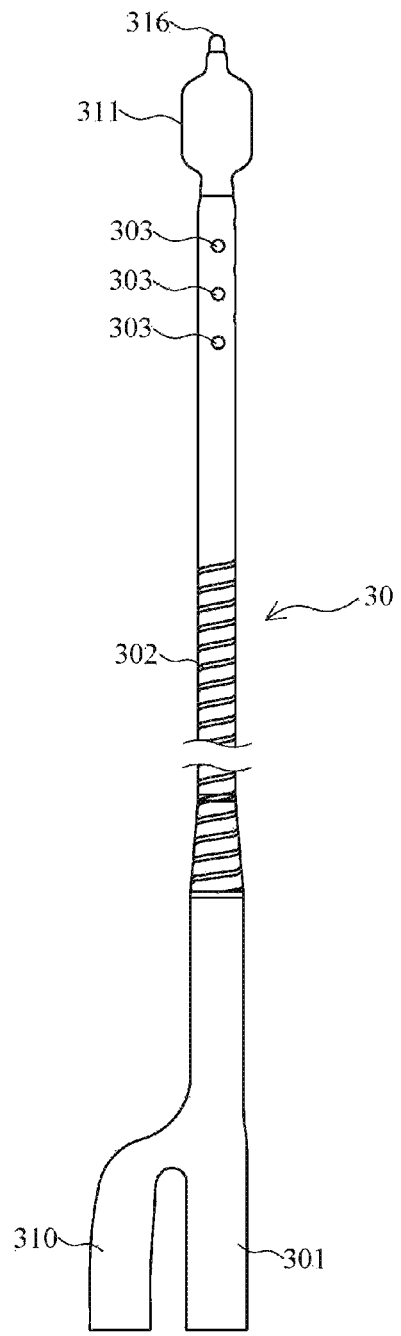

FIGS. 4A and 4B are side views of a drainage cannula assembly according to Embodiment I of the invention.

FIGS. 5A and 5B are longitudinal sectional views of a drainage cannula assembly according to Embodiment I of the invention.

FIG. 5C is a cross-sectional view of the drainage cannula assembly according to Embodiment I.

Figure 6:
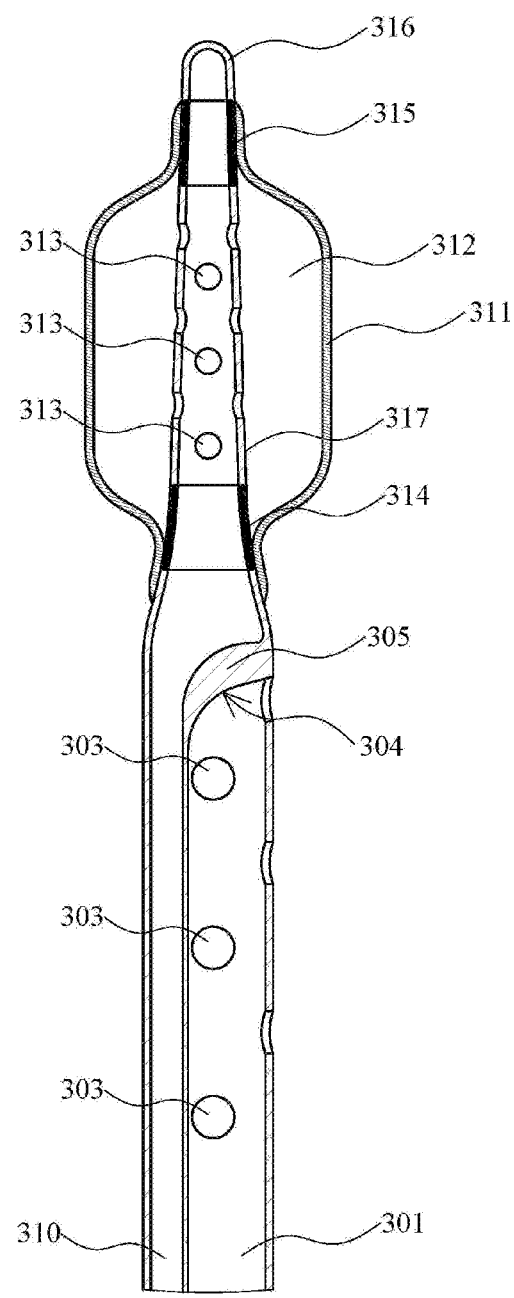

FIG. 6 is a longitudinal sectional view of a balloon of the drainage cannula according to Embodiment I of the invention.

Figure 7:
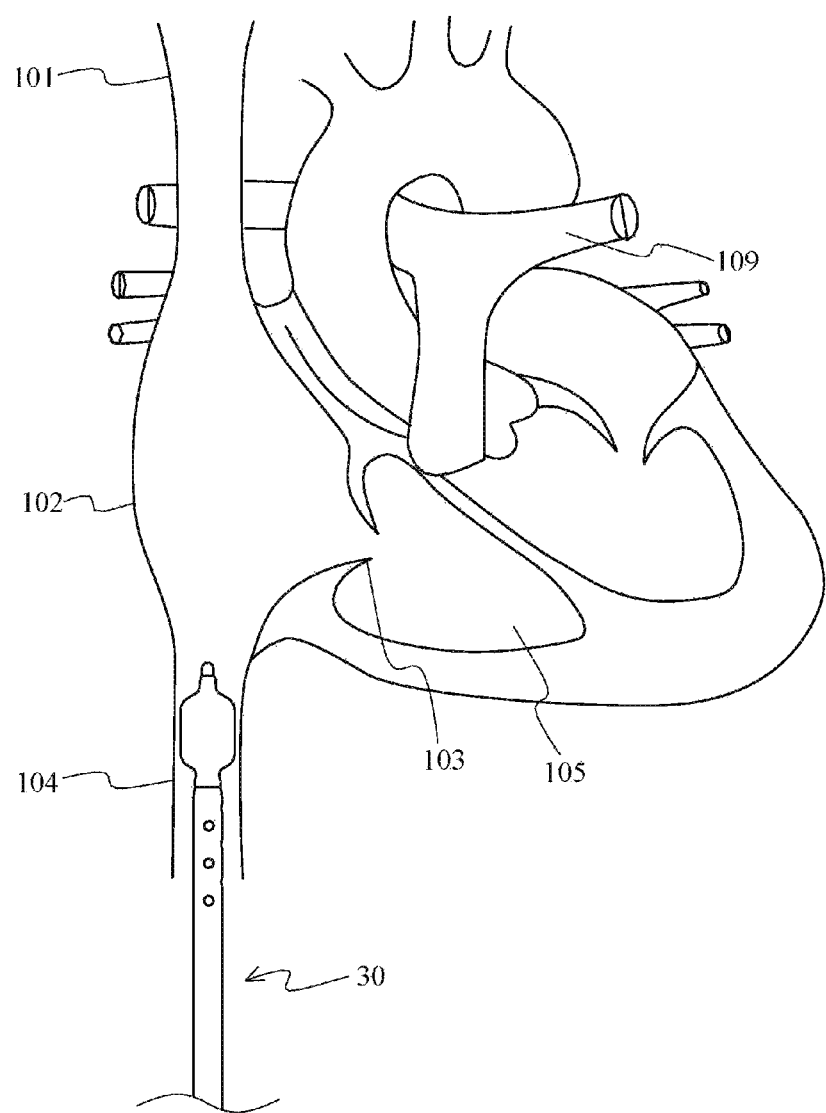

FIG. 7 is a schematic illustration showing the placement of the drainage cannual of Embodiment I disposed in the juncture of IVC and RA.

Figures 8A, 8B:
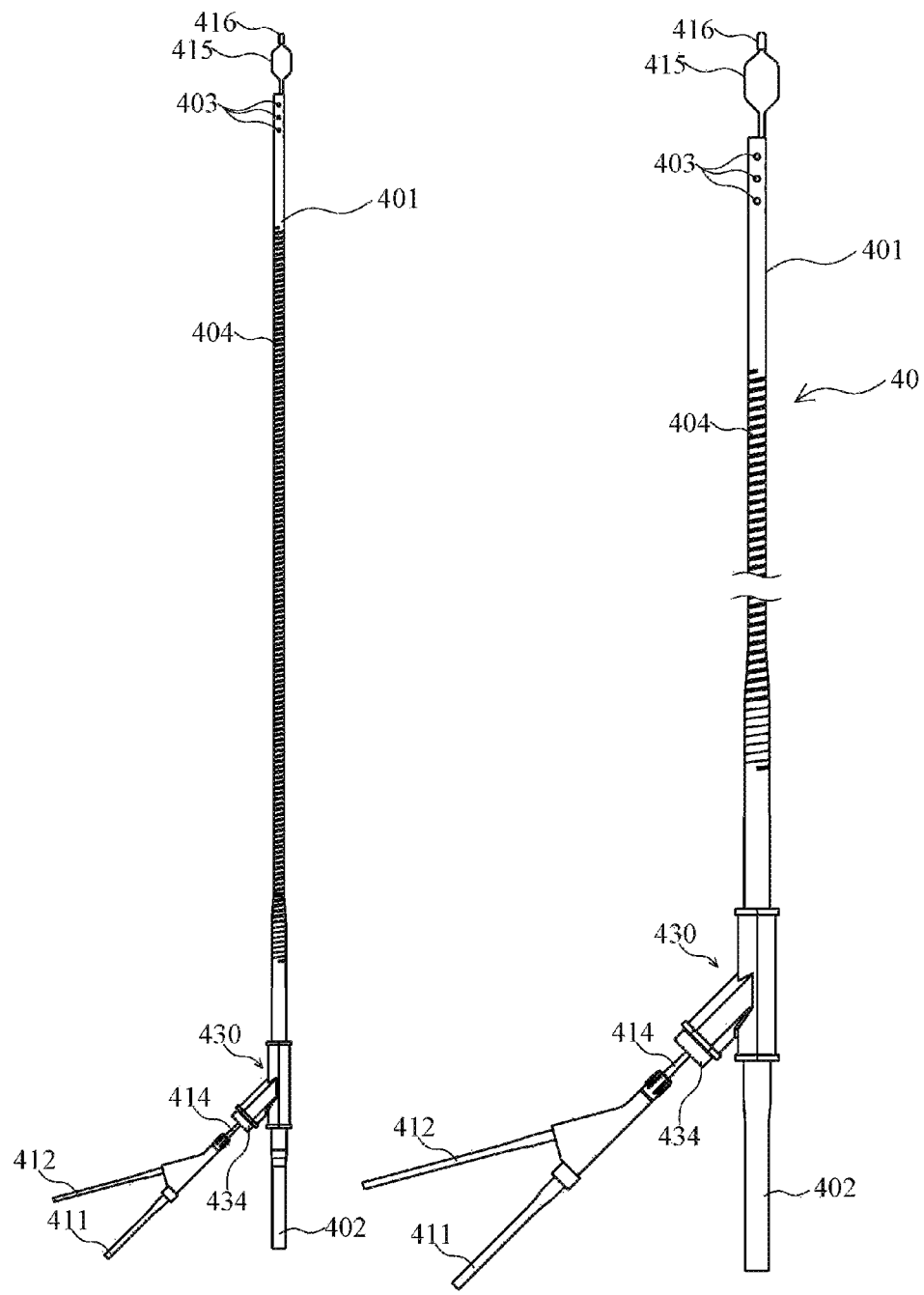

FIGS. 8A and 8B are side views of a drainage cannula assembly according to Embodiment II of the invention.

Figure 9A:
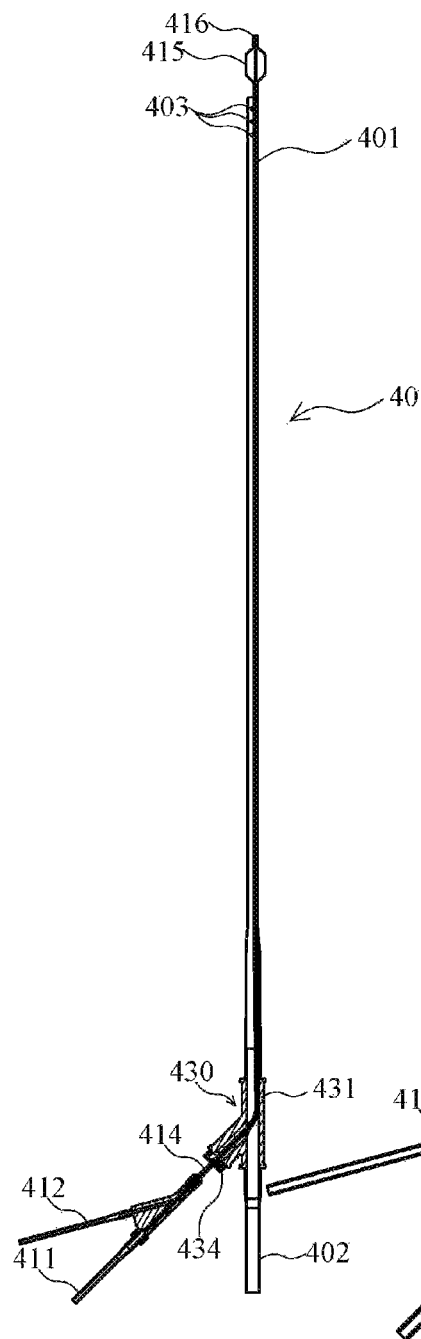
Figure 9B:
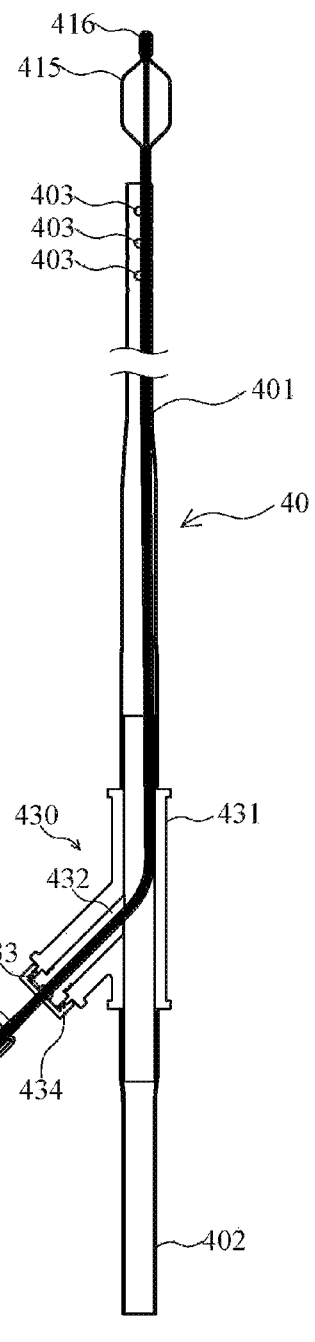

FIGS. 9A and 9B are longitudinal sectional views of the drainage cannula assembly according to Embodiment II of the invention.

Figure 10:
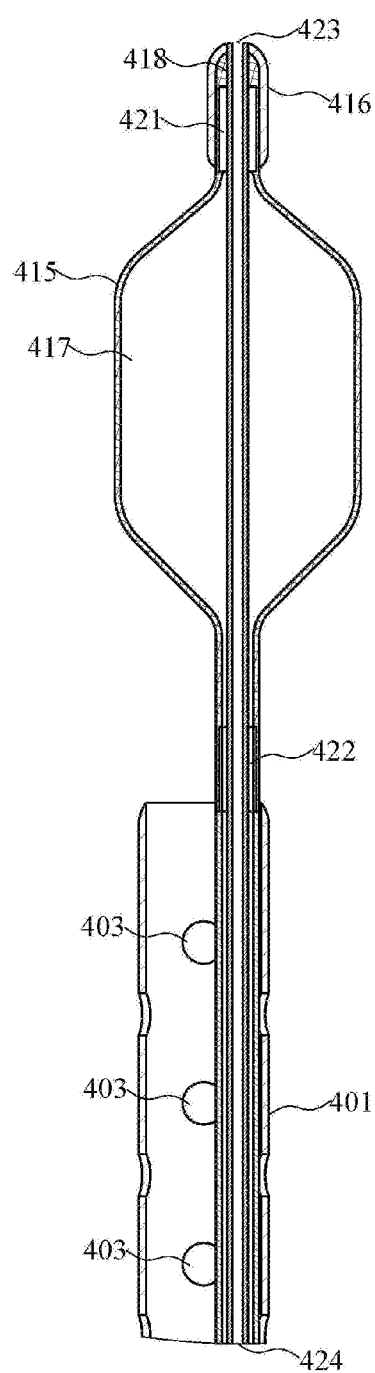

FIG. 10 is a longitudinal sectional view of a balloon of the drainage cannula according to Embodiment II of the invention.

Figure 11:
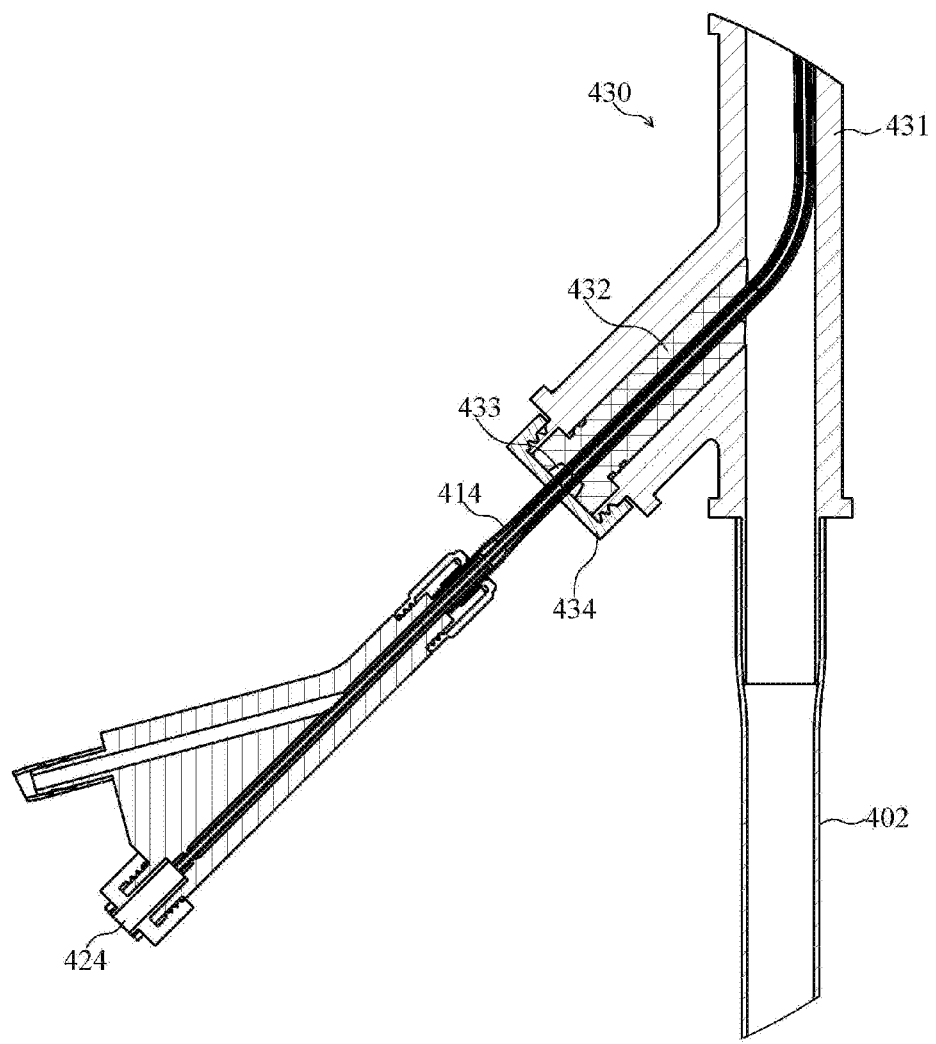

FIG. 11 is a longitudinal sectional view of a drainage Y-connector of the drainage cannula according to Embodiment I of the invention I.

Figure 12A:
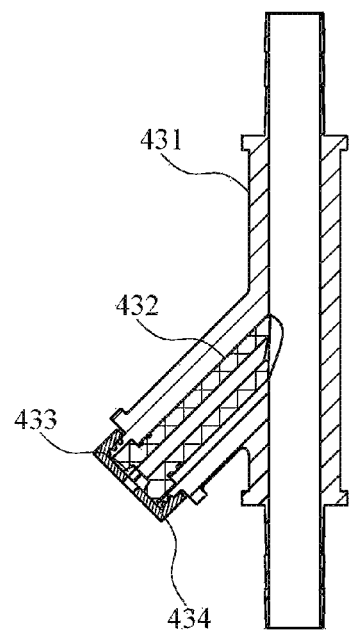

FIG. 12A is a detail illustration of the drainage Y-connector of the drainage cannula according to Embodiment II of the invention.

Figure 12B:
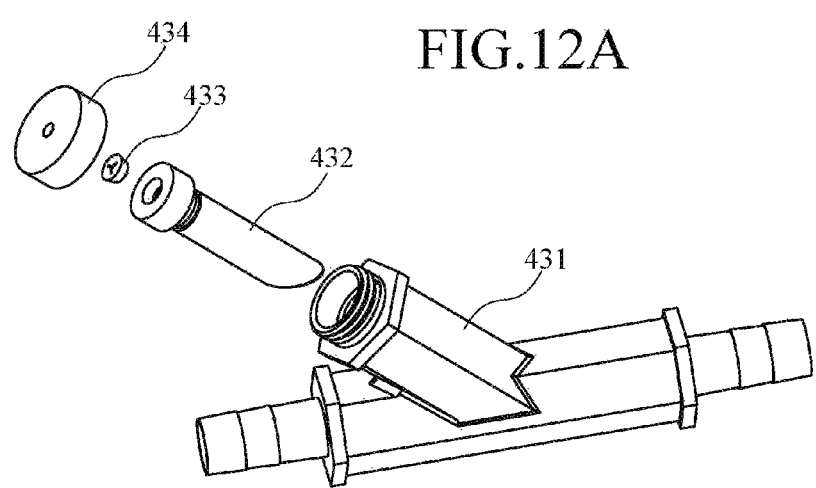

FIG. 12B is an exploded view of the drainage Y-connector of the drainage cannula according to Embodiment II of the invention.

Figure 13:
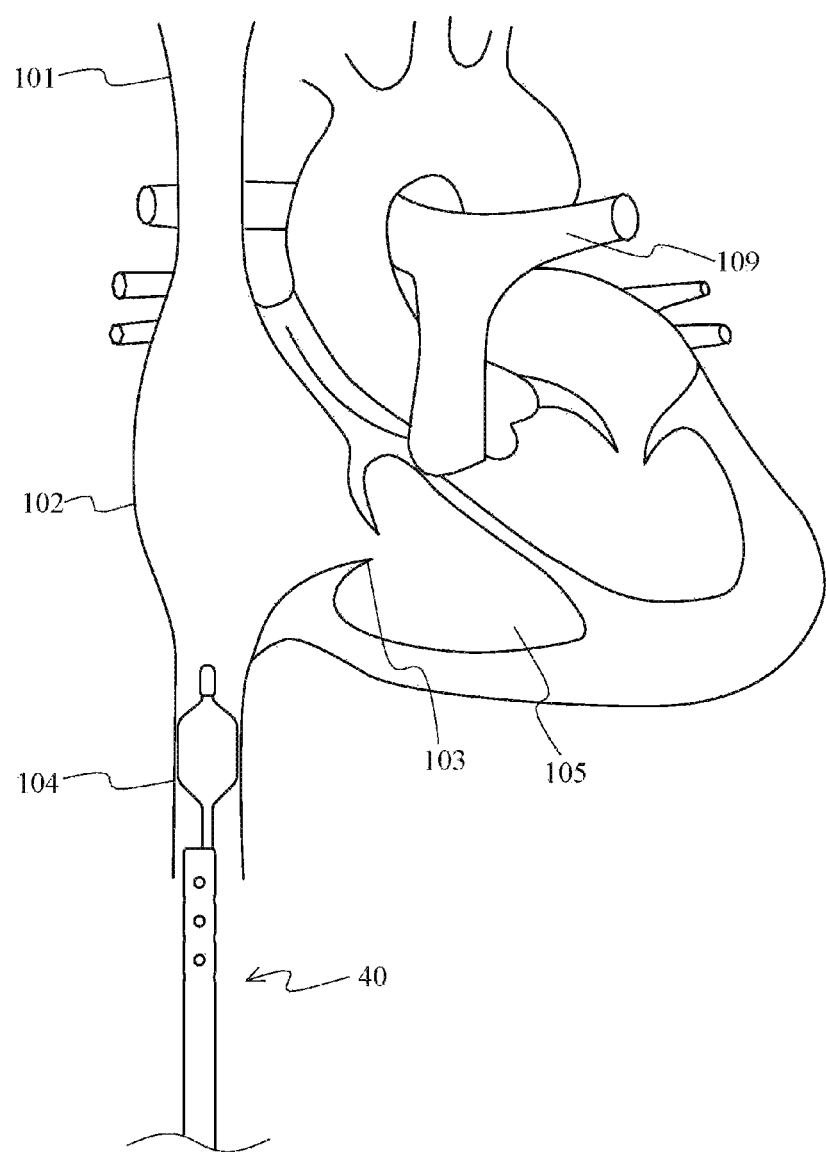

FIG. 13 is a schematic illustration showing the placement of the drainage cannual of Embodiment II disposed in the juncture of IVC and RA.

Figures 14A, 14B:
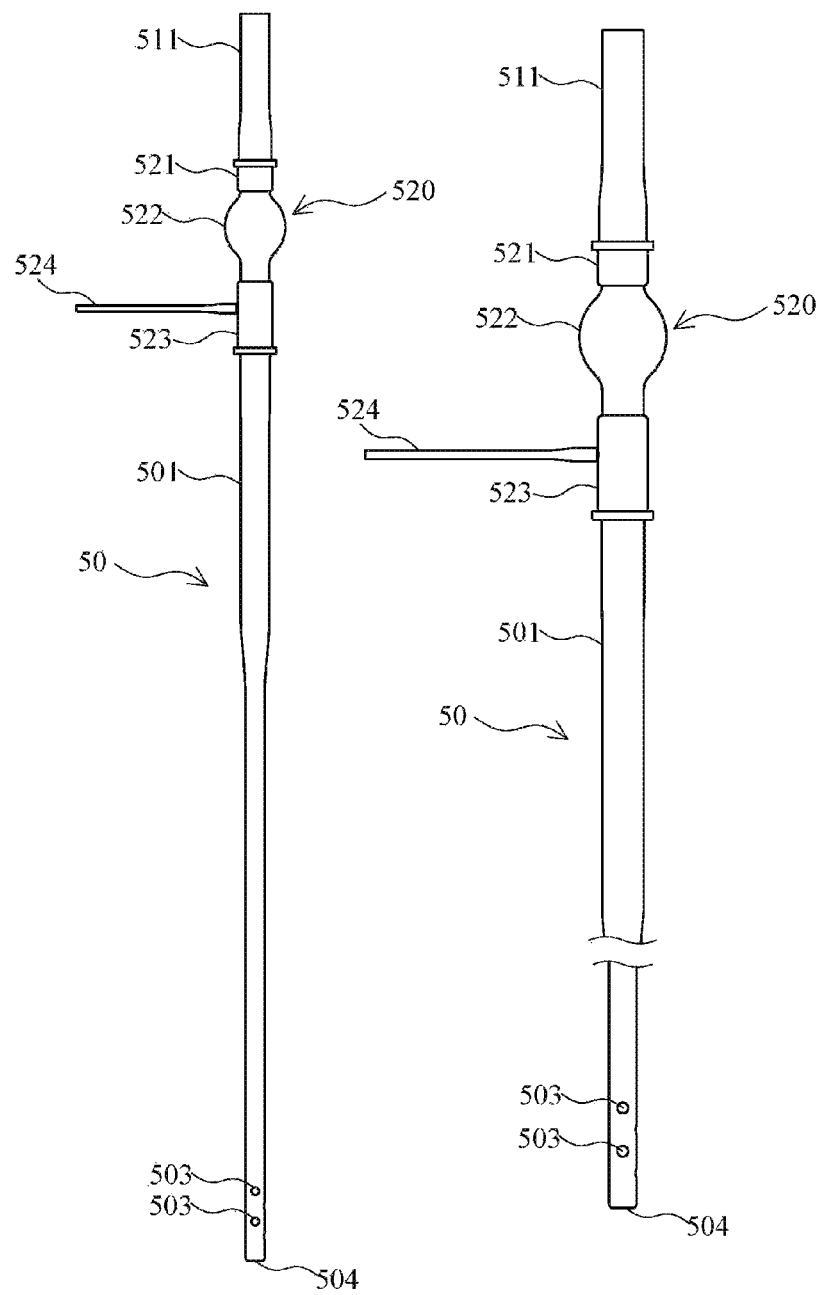

FIGS. 14A and 14B are side views of an infusion cannula assembly according to Embodiment III of the invention.

Figures 15A, 15B:
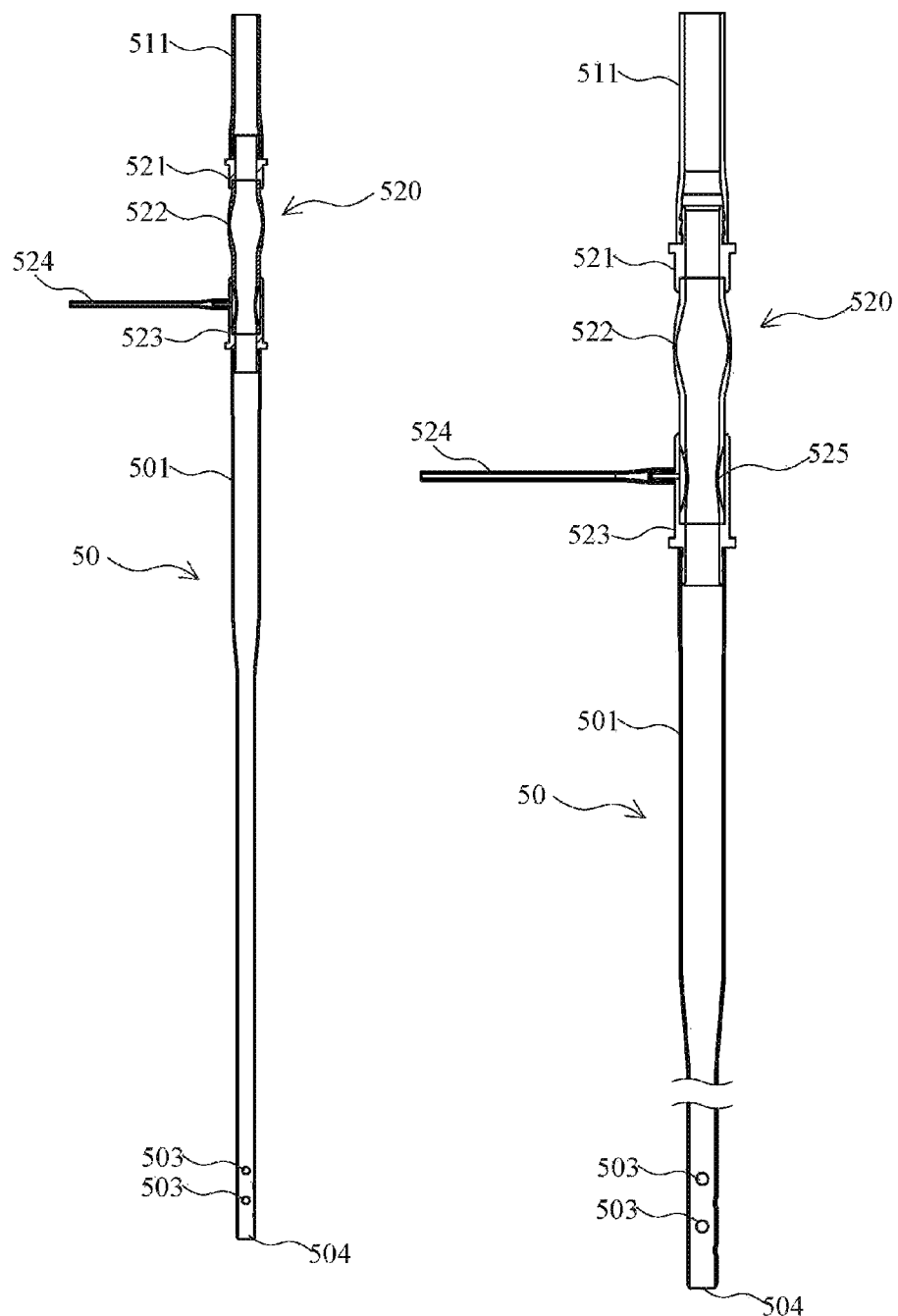

FIGS. 15A and 15B are sectional views of the infusion cannula assembly according to Embodiment III of the invention.

Figure 16:
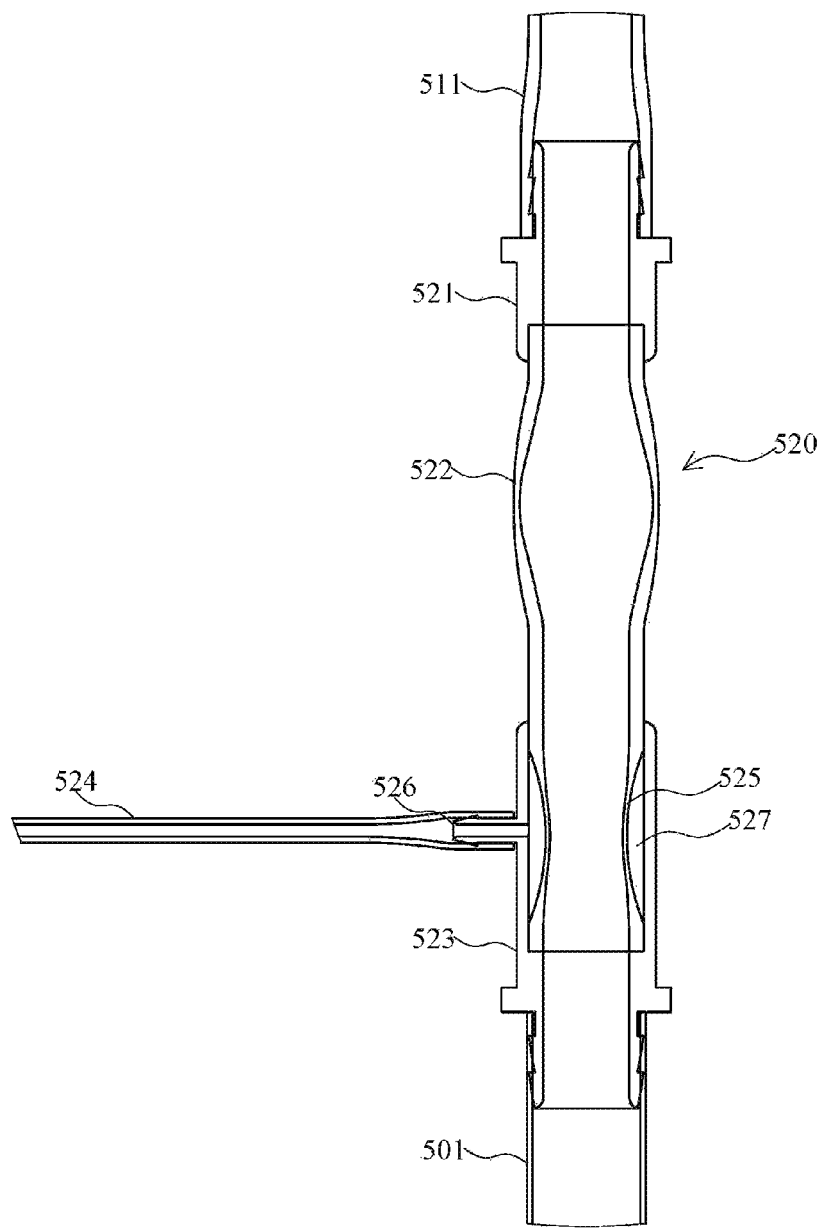
Figure 17:
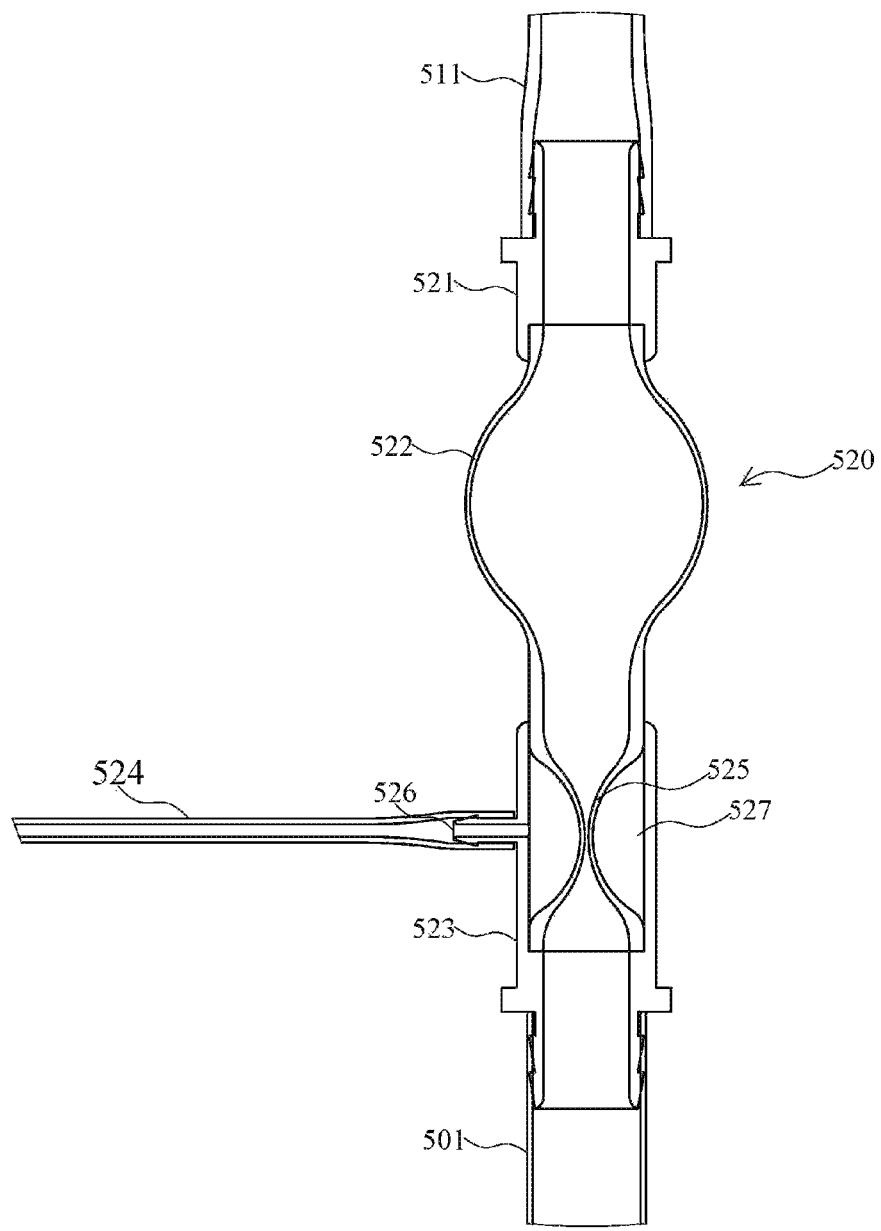

FIGS. 16 and 17 are sectional views of an occlude module of the infusion cannula assembly according to Embodiment III of the invention.

DETAIL DESCRIPTION OF THE PREFERRED EMBODIMENTS

Figure 1:
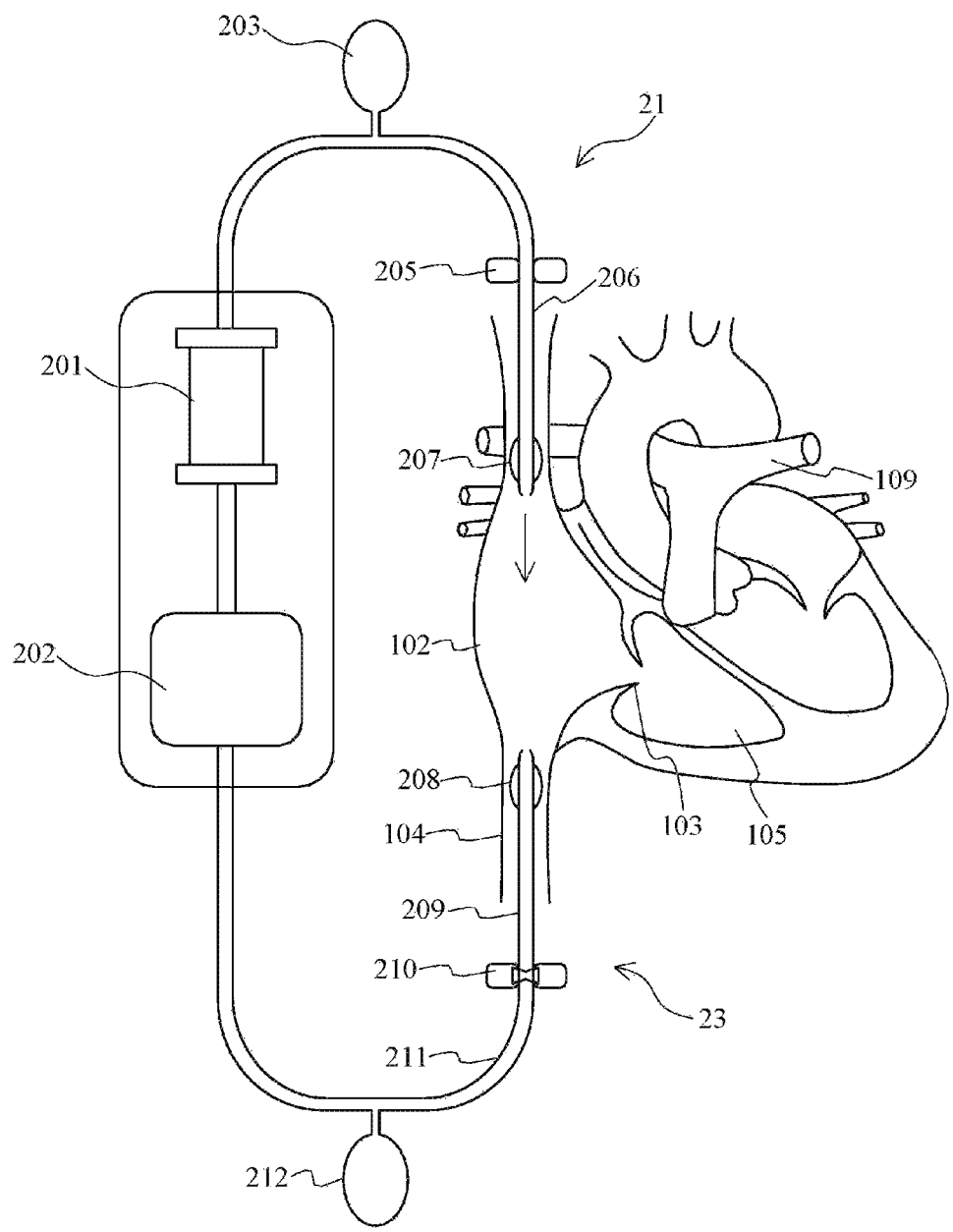
FIG. 1 is a schematic illustrating the VV ECMO circuit in relation to the pulmonary circulation, in which control action characteristic to each of the six flow regulators in the diastolic phase when tricuspid valve is open is presented.
Figure 2:
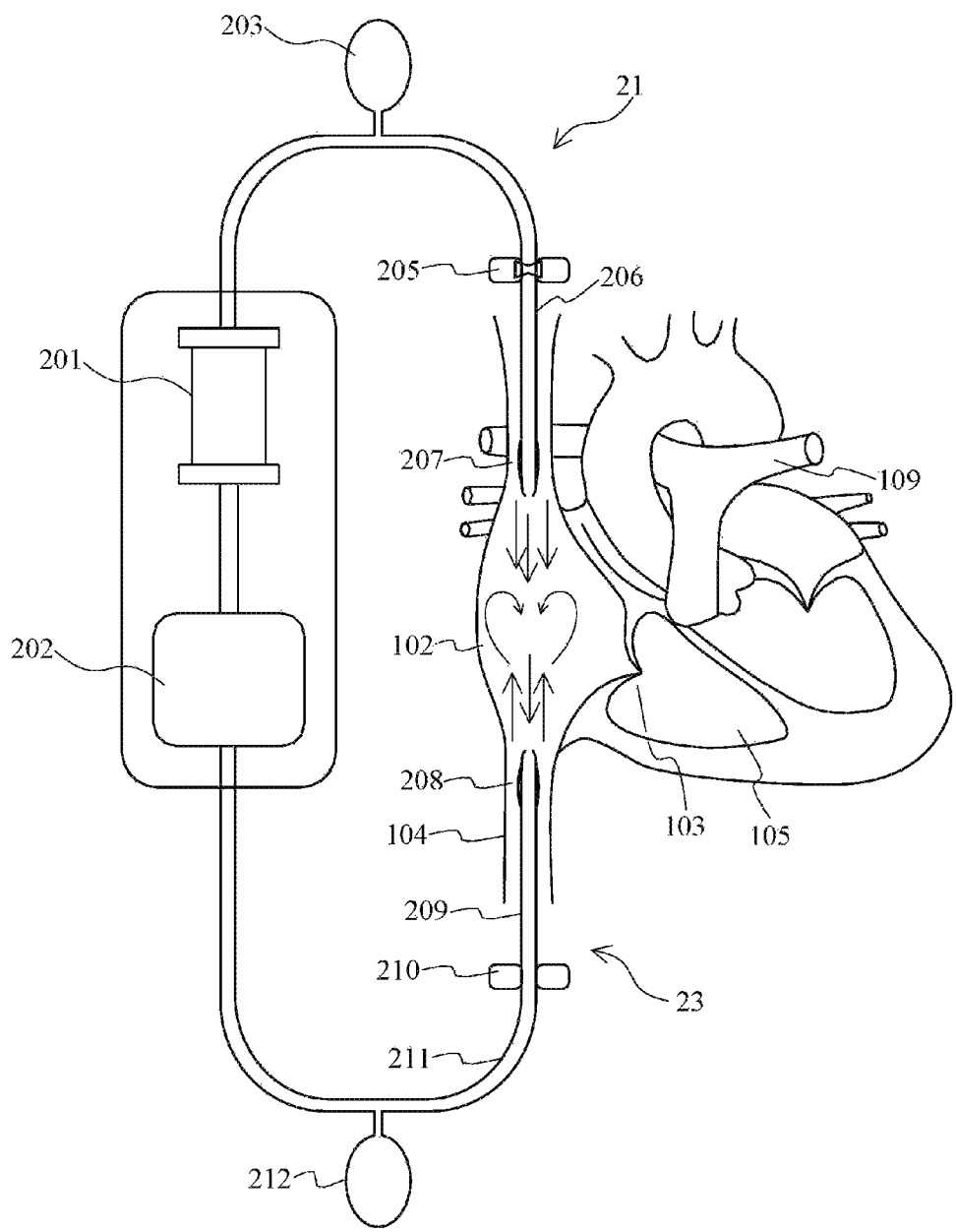
FIG. 2 is a schematic illustrating the VV ECMO circuit in relation to the pulmonary circulation, in which control action characteristic to each of the six flow regulators in the systolic phase when tricuspid valve is closed is presented.

The essence of the present control method is to regulate venous return and ECMO cannula flow in accordance to the tricuspid valve motion. The objective is to minimize the recirculation drawback associated with VV ECMO. FIGS. 1 and 2 illustrate the locations of each disposed control element and the operational mode desired to minimize recirculation occurring respectively in systolic and diastolic phases. FIGS. 1 and 2 are schematic illustrating the VV ECMO circuit in relation to the pulmonary circulation according to an embodiment of the invention. An extracorporeal life support system 20 comprises an oxygenator 201, a blood pump 202, an infusion cannula assembly 21 and a drainage cannula assembly 22. The oxygenator 201 and the blood pump 202 are disposed outside the patient's body. Further, the infusion cannula assembly 21 is placed opposite to the drainage cannula assembly 22. In one embodiment of the invention, the drainage cannula assembly 22 may comprise a drainage balloon 208, a drainage occlude 210 and/or a drainage reservoir 212. In another embodiment of the invention, the infusion cannula assembly 21 may comprise an infusion balloon 207, an infusion occlude 205 and/or an infusion reservoir 203.

In these two figures, drainage cannula 209 is placed in IVC (Inferior Vena Cave) 104, and the drainage balloon 208 is mounted on the drainage cannula 209. The drainage occluder 210 and the drainage reservoir 212 are disposed externally to the patient's body and are connected to the drainage ECMO tubing 211. Likewise, infusion cannula 206, the infusion balloon 207, infusion occluder 205 and infusion reservoir 203, in a similar fashion, are disposed either in SVC (Superior Vena Cava) or outside the body. Note that in surgical settings, infusion cannula 206 and drainage cannula 209 can be reversely exchanged in insertion sites, opposite to the setting disclosed in FIGS. 1 and 2. In practical applications, both cannula assemblies 21, 22 can be actively controlled using the same control method and hardware system presented herein.

The control actions pertaining to the above mentioned flow regulating system are described below.

During the heart diastole phase:

1. During heart diastole, the tricuspid valve 103 between the RA 102 and the RV 105 is open. Prior to tricuspid valve 103 opening, the RA 102 should be filled as much as possible with oxygenated blood preparing for entering RV 105. During tricuspid valve 103 opening, the readily stored oxygenated blood in the RA 102 can maximally flow into and fill up the RV 105. As a result, the RV 105 can be primed with a maximal amount of oxygenated blood which will be ejected into the pulmonary artery 109 and lung to accomplish pulmonary circulation during the subsequent phase of heart systole.

2. In the late systolic phase prior to tricuspid valve 103 opening and during the next diastolic phase when the tricuspid valve 103 opens, the balloons 207, 208 are inflated to obstruct the venous return originated respectively from SVC and IVC 104, and thus preventing the deoxygenated blood from entering the RA 102 while giving room for infusion cannula 206 to flow the oxygenated blood into RA 102.

3. The infusion occluder 205 of the infusion cannula assembly 21 is opened to allow the oxygenated blood from the ECMO outflow end to enter the RA 102. Because of the fact that flow convection and mixing takes time, the "purging" of RA 102 with oxygenated blood should start a bit earlier before the tricuspid valve 103 opens. During this short purging period, both balloons 207, 208 are inflated with the two occluders 205, 210 opened. Thus, the mixed blood stored in RA 102 and the oxygenated blood, stored previously in the infusion reservoir 203 during heart systole, is forcefully expelled, resulting in the maximal filling of oxygenated blood into RA 102 ready for entering RV 105.

4. The drainage occluder 210 on the drainage cannula 209 is closed to prevent the oxygenated blood in the RA 102 from being withdrawn into the ECMO inflow path. At the ECMO drainage site, the drainage occluder 210 closure starts right after the completion of the RA 102 "purging" process and stays closed for most of the diastolic phase. As a result, the recirculation of oxygenated blood back into the ECMO circuit could be additionally reduced.

5. For maintaining a steady ECMO blood pump to operate continuously, the drainage reservoir 212 at the drainage site, which has been passively filled with deoxygenated/mixed blood in the proceeding heart systolic phase, supplies blood mass into the ECMO circuit to feed the blood pump and the oxygenator when the drainage occluder 210 at the drainage site is closed.

During the heart systole phase:

1. During heart systole, the tricuspid valve 103 between the RA 102 and the RV 105 is closed. During this period, the venous return should be maximally drawn into the ECMO draining path and fed by the blood pump to pass through the oxygenator to produce oxygenated blood. Because venous return has been previously impeded during the late diastolic phase, the elevated IVC preload (pressure) would accelerate blood pump flow and hence enhances IVC venous return withdrawal, contributing to oxygenated blood for returning the RA 102 during the next initial diastolic phase.

2. During heart systole, the balloons 208, 207 of both cannula assemblies 21, 22 are deflated, creating a low-pressure suction power to help facilitate venous return from both SVC and IVC 104 to enter and fill the RA 105.

3. The infusion occluder 205 of the infusion cannula assembly 21 is closed to prevent the ECMO oxygenated blood from entering the RA 102. During this ECMO infusion obstruction period, the oxygenated blood will be diverted into the infusion reservoir 203 at the infusion site. Pressure in this infusion reservoir 203 will be elevated accompanying the increased blood volume storage, building a booster pressure gradient that will help eject out the infusion reservoir 203 stored blood when infusion occluder 205 opens during the next heart diastolic phase.

4. The drainage occluder 210 of the drainage cannula assembly 22 is opened for accepting the venous return blood pooled in the RA 102. With the help of the blood pump 202 in action, the blood withdrawn from the drainage cannula 209 will flow through the oxygenator 201 to produce oxygenated blood. Meanwhile, the drainage reservoir 212 of the drainage cannula assembly 22 may additionally be expanded and filled with extra deoxygenated blood during the systolic phase, followed by expelling those stored blood to maintain a steady ECMO flow during the next heart diastole when the drainage occluder 210 at the drainage site is closed.

5. For maintaining the blood pump 202 to operate continuously, the oxygenated blood issued from the ECMO will be passively stored in the infusion reservoir 203 at the infusion cannula assembly 21 as the infusion occluder 205 is closed during the systolic phase. This infusion reservoir 203 stored high-pressure blood will be expelled in a boosted manner during the next diastolic phase when the infusion occluder 205 at the infusion site is opened.

The present invention includes six flow regulators distributed over the drainage cannula assembly 22 and infusion cannula assembly 21 associated with the ECG-gated VV ECMO control system, aiming at minimizing the recirculation rate while maintaining a steady, continuous blood pump operation. For example, the flow regulators may comprise two balloons 207, 208, two occludes 205, 210 and two reservoirs 203, 212. Balloons 207, 208 are intended to regulate the human venous return flow, whereas occluders 210, 205 are used for impeding the ECMO cannula flow over the drainage and the infusion side, respectively. Reservoirs 212, 203 are placed extra-corporeally before the blood pump 202 and after the oxygenator 201, respectively. The control of reservoirs 212, 203 can be either active or passive, depending on the requirements set for maintaining a continuous ECMO pump flow. Balloons 207, 208 are placed in SVC or IVC 104, hence are blood-contacting which should consider suitable hemodynamic configuration design for avoiding hemostasis to occur. Occluders 205, 210 can be installed internally or externally to the cannulas 206, 209, and usually extra-corporeal, non-blood contacting occluder design is preferred. Control logic of an open-loop controller using ECG signal as reference is to be developed. In theory, the present actively-controlled flow regulation system is a single-input and multiple-output controller. The control objective is to minimize the recirculation rate of a VV ECMO system. In the practical design realization, the above-mentioned six actuators (flow regulators) can be all included, partially selected or grouped in various combinations. For each flow regulator, the control-on and control-off timings relative to ECG waveform are set as the control parameters. Collectively, all the control parameters included in the selected flow regulators will be optimized simultaneously so as to minimize the recirculation rate.

Illustrated in FIG. 3A is the control block diagram of the present invention. Heart rhythm, typically ECG waveform, is continuously received by a data acquisition system augmented by an algorithm that can detect the onset of heart systole, namely the R-wave. FIG. 3B schematically depicts the triggering timing (control-on or control-off) associated with each flow regulator. Jump-up and jump-down on the square-wave time series shown in FIG. 3B represent the control-on and control-off of the regulator, respectively. For each flow regulator, turning on or off of the regulator is timed relative to the R-wave. Time delays relative to this R-wave are predetermined control input parameters. There are maximally 12 control variables involved in this active control system. Commanding the control-on and control-off of the corresponding flow regulators may include, in full or in partial as a combinatory group of those balloons, occluders, and reservoirs mounted on the drainage and infusion cannula assembly of the ECMO system. Assessment of recirculation can be conducted using mock circulation loop or animal experiment. By iteratively searching for the best set of control input parameters that minimizes recirculation rate, the optimized triggering algorithm can be found and implemented in the present VV ECMO invention.

In one embodiment of the invention, an extracorporeal flow regulator system may comprises a pneumatic pumping mechanism, a sensing system that can receive signal characterizing heart rhythm, a controller that can generate command according to an implemented control logic and the sensed heart rhythm signal. The control logic is optimized to maximize oxygenated blood entering right ventricle during heart diastole, and is optimized to maximize the deoxygenated venous return being drained into the life support circuit during heart systole.

Embodiment I, Drainage Cannula Equipped with Attached Balloon

FIGS. 4A and 4B are side views of a drainage cannula assembly according to Embodiment I of the invention. FIG. 4A shows a 1:1 scale proportion of the drainage cannula assembly, and FIG. 4B is an amplified view of FIG. 4A. Embodiment I, illustrating the installation of balloon, drainage side holes on the drainage cannula assembly. FIGS. 5A and 5B are longitudinal sectional views of a drainage cannula assembly according to Embodiment I of the invention. FIG. 5C is a cross-sectional view of the drainage cannula assembly according to Embodiment I, of which a smaller lumen assigned for control air and a larger lumen assigned for blood flow are illustrated. FIG. 6 is a longitudinal sectional view of a balloon of the drainage cannula according to Embodiment I of the invention, in which balloon attachment, air flow orifice, blood drainage side holes and radiopaque markers are illustrated. Similar components appearing in different views are labeled similarly throughout the descriptions.

The drainage cannula assembly 30 generally includes two fluid passages. One fluid passage is able to transmit or withdraw blood, another fluid passage is connected to the drainage balloon 311 to drive the drainage balloon 311 inflation or deflation. For example, these two fluid passages may be a drainage cannula 301 and a drainage air catheter 310. The drainage cannula 301 forms a first lumen and the drainage air catheter 310 forms a second lumen. For example, the drainage air catheter 310 may be disposed within the drainage cannula 301. In at least one embodiment, each of the drainage cannula 301 and the drainage air catheter 310 has a portion of its side wall merges into a side wall, and a septum separating the lumens, of the drainage cannula assembly 30. One end, such as the lower (proximal) end, of the drainage cannula 301 can be coupled to ECMO tubing conveniently by, for example, a barbed quick connector. The other end, such as the upper (distal) end, of the drainage cannula 301 terminates with a sealed cannula end 316. A drainage balloon 311 is mounted externally on the side wall of a conical extension 317 near the sealed cannula end 316 of the drainage cannula 301. Pneumatic communication of drainage balloon volume 312 with its designated extracorporeal controller system is accomplished via the drainage air catheter 310, further communicated with the conical extension 317 on which side holes 313 are drilled. The drainage air catheter 310 is split from the drainage cannula assembly 30 at a location distal to the sealed cannula end 316. For example, the drainage cannula 301 and the drainage air catheter 310 are disposed at one end of the drainage cannula assembly 30 with sealed cannula end 316. The drainage balloon 311 and the side holes 303 are disposed over the tip region of the drainage cannula assembly 30. For the air catheter 310, the side holes 313 are disposed within the drainage balloon 311, and are near the sealed cannula end 316. The split juncture of the drainage air catheter 310 is separated with a proper distance relative to the skin incision location where the drainage cannula assembly 30 exits outside of the patient's body. In the present illustrated embodiment, the merging transition zone is strengthened and protected by the bifurcated structural body of the drainage cannula assembly 30 having thicker wall.

Multiple openings or drainage holes 303 are disposed along the length of the drainage cannula 301. The drainage holes 303 are distributed over a segment beneath the drainage balloon 311. The array of drainage holes 303 is best formatted in a staggered manner for a maximal withdrawal of the venous return blood. The cannula wall 302 in between the drainage hole array and the split transition zone is wire-reinforced using polymeric or metal wires. Since the cannula end 316 is sealed, the drainage holes 303 on the side wall of the drainage cannula 301 should have a smooth internal intake ramp 304 to seal off the terminal cannula end 305 and thus avoid any hemostasis to occur locally around the drainage hole 303.

The drainage balloon 311 is externally mounted over the conical extension 317 attached to the sealed cannula end 316 of the drainage cannula assembly 30, as shown in FIG. 6. Indicators 314, 315 on the two sides of the drainage balloon 311 are coupled to the drainage cannula 301 and are made of radiopaque material either bonded to or material integrated with the drainage cannula 301. Polymeric material such as, but not limited to, silicone or polyurethane can be used to manufacture the balloon. The balloon volume 312 can be 3-15 c.c. depending on the size of the vessel to be inserted and the blockage ratio that is intended to achieve when the drainage balloon 311 is inflated to obstruct the venous return. Pneumatic communication of the drainage balloon 311 with the designated controller is accomplished via the drainage air catheter 310 with one end terminated at the flow regulator side and another connected to the conical extension 317, in which the decompressed or compressed air is moved back and forth to deflate or inflate the drainage balloon 311 according to the control command.

Blood is to be drained from the drainage cannula 301 disposed either in SVC or IVC. The relative insertion position of the present drainage cannula, as placed in the juncture of IVC 104 and RA 102, is shown in FIG. 7.

The present embodiment is a variant of the working principle illustrated in FIGS. 1 and 2. Notice that in FIGS. 1 and 2, blood comes into ECMO circuit via the end of drainage balloon 311 distal to the balloon only, whereas a reservoir 212 is needed to work in conjunction with the drainage occluder 210 to regulate the ECMO circuit flow. In the present embodiment of a sealed cannula end 316 and a drainage hole 303 array distributed near the drainage balloon 311, the reservoirs 212, 203 and/or the occluders 211, 205 can be omitted to simplify the hardware realization and the control design as well.

As the drainage balloon 311 is expanded to obstruct oxygenated/mixed blood flowing from the RA 102, the sealed cannula end 316 helps prevent the oxygenated/mixed blood from being sucked into the ECMO circuit, thus reducing the undesirable recirculation. Despite drainage balloon 311 inflated, deoxygenated venous return can still be continuously withdrawn from those multiple drainage holes 303 during heart diastolic phase. There exists no time period that drainage of venous return would be completely shut down that necessitates the reservoir operation to maintain a non-stop, continuous ECMO pumping operation. In the present embodiment, controlling cannula flow occlusion and regulating venous return is, in fact, fused into one mechanism of a sealed-end balloon cannula control. As the drainage balloon 311 inflated, blood drainage is facilitated by drainage holes 303 that withdraw SVC or IVC venous return flow depending on where the drainage cannula 209 is placed. As the drainage balloon 311 deflated, both IVC and SVC venous return flows could be withdrawn into the present drainage cannula 209. The drainage balloon 311 also serves as a flow blocker to impede the re-circulated RA chamber flow. Accompanying the drainage balloon 311 inflation, local high-pressure resulting from flow deceleration/blockage created by the drainage balloon 311 obstruction will divert the infused oxygenated blood flow toward the tricuspid valve 103, and this flow direction alteration may lead to a maximal RV priming of the oxygenated blood supposed that balloon expansion timing is properly controlled in accord with the RV muscular relaxation and tricuspid valve opening, collectively creating a "push-and-pull" driving power for RV to receive the accelerated RA priming flow.

An ordinary market available single-lumen infusion (no moving parts or flow regulators mounted) cannula can be used to work with the present drainage cannula embodiment and hitherto constitute a low-recirculation VV ECMO circuit. Such an arrangement, actually, is the simplest actively-controlled VV ECMO setting.

Embodiment II, Drainage Cannula Equipped with Loosely Coupled Balloon

FIGS. 8A and 8B are side views of a drainage cannula assembly according to Embodiment II of the invention, illustrating the relationship of a balloon catheter as inserted into a single-lumen drainage cannula. FIG. 8A shows a 1:1 scale proportion of the cannula assembly, and FIG. 8B is an amplified view of FIG. 8A. A drainage cannula assembly 40 comprises a drainage cannula 401, a drainage air catheter 414, and a drainage Y-connector 430. FIGS. 9A and 9B are longitudinal cross-sectional views of a drainage cannula assembly according to Embodiment II of the invention, illustrating detail interior relationship of drainage air catheter when disposed inside the cannula assembly. FIG. 9A shows a 1:1 scale proportion of the cannula assembly, and FIG. 9B is an amplified view of 9A. The drainage cannula 401 is coupled with the drainage air catheter 414 and the drainage Y-connector 430. Actively-controlled flow occluder providing venous return flow regulation is facilitated by a drainage balloon 415 and the drainage air catheter 414, whose structural relationship is shown in FIGS. 9A and 9B. FIG. 10 is a longitudinal sectional view of a balloon of the drainage cannula according to Embodiment II, in which balloon attachment, air flow orifice, blood drainage side holes and radiopaque markers are illustrated. FIG. 11 is a longitudinal sectional view of a drainage Y-connector of the drainage cannula according to Embodiment II, showing the drainage air catheter introduction passage and the hemostasis control provided by the Y-connector. The drainage Y-connector 430, illustrated in detail in FIGS. 11, 12A, and 12B, constitutes an insertion adaptor for drainage air catheter to be delivered into the drainage cannula without blood leakage and air ingression.

The drainage cannula assembly 40 is a thin-walled tube made of biocompatible polymeric material such as, but not limited to, polyurethane or silicone. In the present embodiment the cannula tip 416 is open, and in close proximity to this cannula tip opening 416 reside multiple drainage holes 403 drilled and distributed along the wall of the drainage cannula 401. These drainage holes 403 are made to maximally draw the venous return flow no matter if the drainage balloon 415 is inflated or deflated. In order to achieve a less traumatic surgical insertion, the cannula wall is thin and comprises wire-reinforced unit 404, allowing a smooth, kinking-free insertion to be accomplished. The gradually enlarged lower portion of this drainage cannula assembly 40 is intended to reduce flow resistance, which can also provide a structural transition and coupling to the drainage Y-connector 430.

An inserted drainage air catheter 414 in the drainage cannula assembly 40 is depicted in FIGS. 9A and 9B. The drainage air catheter 414 is generally straight before insertion, but the flexural property of the drainage air catheter 414 can allow the drainage air catheter 414 to curve along its deployment path. The drainage air catheter 414 can generally comprise an inner (pressure-sensing) tube 411 and an outer (air delivery) tube 412, with the inner tube 411 longitudinally disposed within the outer tube 412. Around the upper end of this drainage air catheter 414 is a drainage balloon 415 that is made of polymeric material such as polyurethane or silicone. The drainage balloon 415 can be inflated or deflated as controlled by the extracorporeal actuator system. Shown in FIGS. 8A, 8B, 9A, 9B and 10 is a fully expanded drainage balloon 415 with its shape conformal to the dipping mandrel or the mold from which it is blown molded. The drainage balloon 415 is seamlessly bonded or coupled to the drainage air catheter 414. In FIG. 10 shows a preferred balloon integration method illustrating a seamless adhesive bonding of a distal tubular balloon end with the inner tube 411 and a proximal tubular end with the outer tube 412. The inner tube 411 is typically having a size around 1 mm in outside diameter. Saline fluid can be injected to fill up this inner tube space 424 to form a hydraulic pressure sensing channel, and extended to a tip hole 423 for facilitating measurement of the vena cava blood pressure during ECMO support. Pneumatic communication between a balloon volume 417 and an extracorporeal controller is accomplished using the lumen space in between the inner tube 411 and the outer tube 412. To help drainage balloon 415 in place during insertion, radiopaque markers are disposed at the proximal 422 and distal 421 tubular ends of the balloon 415. Cannula tip 416 is encapsulated by a cap over the distal end of the inner tube 411, forming a smooth profile to protect the vessel from being injured during catheter deployment.

The drainage Y-connector 430 generally comprises a Y-shaped main-body 431, a hemostasis Y-slit taper 433, a plug 432, and a lock cap 434, as depicted in FIGS. 12A and 12B. The first arm of the drainage Y-connector 430 is bilaterally coupled to the drainage cannula 401 and the ECMO tubing 402, respectively, together constituting a blood drainage passage for drawing venous return from either IVC or SVC. The plug 432 is disposed in the second arm of the drainage Y-connector 430, which, as works together with Y-slit taper 433, generates a sealing mechanism for drainage air catheter 414 deployment and installation. Plug 432 and Y-slit taper 433 are generally made of elastic, deformable polymeric material such as silicone or rubber. This plug 432 has one side flush mounted relative to the drainage cannula inner wall. A smooth, continuous hydrodynamic interface is generally required for constructing this blood-contacting plug surface where the drainage air catheter 414 enters the drainage cannula 401. The objective is to minimize possible blood clot to be formed at the surface discontinuities around the catheter-cannula interface. On the other end of this plug 432 houses a Y-slit taper 433 that is intended to work as a hemostasis valve.

The drainage air catheter 414 deployment is carried out by first inserting the drainage air catheter 414 through the Y-slit taper 433, and then pushing the drainage air catheter 414 through against the channel wall of the plug 432. Appropriate clearance between the outer wall of the drainage air catheter 414 and the channel of the plug 432 should be designed to accomplish a smooth but non-leaking balloon catheter deployment. A lock cap 434 is screw-connected with the Y-shaped main-body 431, as shown in FIG. 11. By turning screw turns, this lock cap 434 can provide different sealing effectiveness by exerting controlled compression force on the hemostasis Y-slit taper 433. During drainage air catheter 414 insertion, the lock cap 434 is first loosened to help the drainage air catheter 414 and the drainage balloon 415 engagement. Hemostasis is then guaranteed by the compressed taper 433 resulting from cap tightening, which seals off blood regurgitated from the catheter-cannula interface rim during drainage air catheter 414 insertion. As ECMO pump is running, negative pressure gradient along the cannula length is generated for blood withdrawal. The blood pressure around the drainage Y-connector 430 is generally lower than the atmospheric pressure. Hence, a tight sealing provided by the hemostasis Y-slit taper 433 is necessary for preventing ambient air to be sucked into the blood stream. Failure of a tight taper seal may endanger the patient with life threatening air embolism.

In the practical application of the present Embodiment II, cannulation procedure is accomplished in two steps. The first step is to implant the drainage cannula 401 using a tool set of needle, guide wire, and introducer. This procedure is the same common practice surgeons are performing clinically for inserting single-lumen cannula of an ECMO system from either the IVC or the SVC site. The second step is to deploy the drainage air catheter 414. The balloon 415 on the drainage air catheter 414 is deflated into a smaller profile ready for insertion through the hemostasis Y-slit taper 433 inlet. The lock cap 434 is first loosened to help receive the drainage air catheter 414, and then tightened after the drainage air catheter 414 clears the plug 432, advances along the drainage cannula 401, and finally arrives at the desired location where drainage balloon 415 is properly placed outside the opening of the cannula tip 416. Imaging system can be used to result in an accurate navigation so as to accomplish the Step 1 and 2 placements. FIG. 13 illustrates the insertion and placement of the present Embodiment II in the IVC and RA juncture.

Embodiment III, Infusion Cannula Equipped with Occluder

The present Embodiment III infusion cannula assembly 50 is schematically illustrated in FIGS. 14A and 14B. FIG. 14A shows a 1:1 scale proportion of the cannula assembly, and FIG. 14B is an amplified view of 14A. FIGS. 15A and 15B are sectional views of the infusion cannula assembly of Embodiment III, illustrating the detail integration of occluder, reservoir in relation to the infusion cannula and ECMO tubing. FIG. 15A shows a 1:1 scale proportion of the infusion cannula assembly, and FIG. 15B is an amplified view of FIG. 15A. The infusion cannula assembly 50 comprises an infusion cannula 501, an occluder module 520, a pneumatic line 524, and an ECMO tubing 511, wherein the occluder module 520 is serially connected between the infusion cannula 501 and the ECMO tubing 511, respectively. The occluder module 520 comprises an occluder 525 disposed in an occluder chamber 523 and a reservoir 522. In one embodiment of the invention, the occluder 525 is connected to the infusion cannula 501, and the reservoir 522 is connected to the ECMO tubing 511. The infusion cannula 501 is a common single-lumen cannula, such as the one disclosed in Embodiment II. The occluder (infusion occluder) 525, 205, 210 and the (infusion) reservoir 522, 203, 212 may be aligned in series to minimize the flow resistance, wherein the infusion flow control may be regulated by compressing or expanding the occluder (infusion occluder) 525, 205, 210 cross-section with passive reservoir 522, 203, 212 engaged in response to the occluder (infusion occluder) 525, 205, 210 motion to result in a continuous blood pump flow in the life support system. The tip opening 504 and the side holes 503 drilled on the infusion cannula 501 are provided for blood flow infusion. For example, the tip opening 504 is disposed on one end of the infusion cannula 501, and the side holes 503 are disposed on the side wall of the infusion cannula 501. The occluder 525 presently designed for impeding the blood flow in the infusion cannula 501 is a flexible conduit having distributed wall thickness. As this conduit is subject to air compression the infusion occluder 525 housed in the occluder chamber 523 will be pinched with cross-sectional area decreased to impede the infusion blood flow. Meanwhile, the infusion reservoir 522 will be responsively expanded to receive the occluded flow volume, enabling a continuous running of the ECMO circuit flow. The present Embodiment of the infusion flow control, in fact, combines the functions associated with occluder and reservoir operations explained and shown in FIGS. 1 and 2. The reservoir volume passively responses in conjunction with the active occlusion flow control provided by an extracorporeal flow regulating system.

The detailed construction of this flow occluder module is depicted in FIGS. 16 and 17. FIG. 16 illustrates the occluder and reservoir operation during heart diastole, of which occluder is in its full opening state while reservoir remaining not stretched. FIG. 17 illustrates the occluder and reservoir operation during heart systole, of which occluder is in its fully closed state while reservoir being largely expanded to receive the ECMO circuit flow. The present occluder subsystem generally comprises a barbed adaptor 521, an occluder module 525, a pneumatic chamber 527, and a pneumatic line 524 coupled to the pneumatic chamber 527 at the barbed adaptor 526. Control of occluder module 525 is commanded by facilitating air communication with the extracorporeal flow regulating system. The ECMO tubing 511 is coupled onto the occluder module 520 via the barbed adaptor 521. The occluder 525 of the occluder module 520 is coupled without leakage concern to the two ends of the pneumatic chamber 527. The chamber structure is rigid or semi-rigid as compared to the flexible conduit. The cross-sectional area of the occluder 525 can thus be controlled as the pneumatic chamber pressure is regulated. The infusion cannula 501 is coupled to the distal end of the occluder chamber 523 where barbs are implemented for a quick cannula connection.

The extracorporeal life support system of above embodiment of the invention may only comprise a balloon 207, 208, 311, 415, an occluder (module) 205, 210, 525 or a reservoir 203, 212, 522. The balloon 207, 208, 311, 415, the occluder (module) 205, 210, 525 and/or the reservoir 203, 212,522 can be actuated according to the patient's heart rhythm to maximize the oxygenated blood entering right ventricle during heart diastole, together with deoxygenated venous return being drained into the life support circuit during heart systole.

The present invention may be embodied in other specific forms without departing from its fundamental control principle herein disclosed and explained. The described embodiments are to be considered in all respects only as illustrative and not restrictive. All changes which come within the meaning and range of equivalency of the claims are to be embraced within their scope.

The invention claimed is:

1. An extracorporeal life support system comprising:
   a blood pump and an oxygenator disposed outside a patient's body;
   a drainage cannula assembly disposed in superior vena cava or inferior vena cava to receive deoxygenated blood, comprising at least one of a drainage balloon, a drainage occluder and a drainage reservoir that are employed and actuated in accordance with the patient's heart rhythm, wherein the drainage balloon is inflated or deflated to control venous return blood flow, the drainage occluder is compressed or relaxed to control blood drainage into the extracorporeal life support system, and the drainage reservoir is actuated together with the drainage occluder to result in a continuous blood pump flow; and
   an infusion cannula assembly disposed opposite to the drainage cannula assembly in either the superior vena cava or the inferior vena cava, the infusion cannula assembly being employed to deliver oxygenated blood flow back to the patient's circulation,
   wherein the drainage cannula assembly comprises a drainage cannula, a drainage air catheter and a drainage Y-connector, and the drainage air catheter is connected to the drainage balloon and physically separated from the drainage cannula, wherein the drainage cannula comprises a cannula tip and a plurality of drainage holes distributed at one end of the drainage cannula, wherein the drainage cannula is coupled to a first arm of the drainage Y-connector, and a plug is equipped on a second arm of the drainage Y-connector for receiving the drainage air catheter insertion.

2. The extracorporeal life support system as claimed in claim 1, wherein the drainage cannula assembly comprises two fluid passages, one fluid passage is able to transmit blood, another fluid passage is connected to the drainage balloon to drive the drainage balloon inflation or deflation, and the two fluid passages are separated and are not fluid communicated to each other.

3. The extracorporeal life support system as claimed in claim 2, wherein the drainage cannula assembly comprises a sealed cannula end disposed on one end of the drainage cannula assembly, and a plurality of drainage holes disposed on a side wall of the drainage cannula assembly and near the sealed cannula end.

4. The extracorporeal life support system as claimed in claim 1, wherein the drainage air catheter comprises an inner tube and an outer tube, the outer tube is used for pneumatic control of the drainage balloon inflation or deflation, and the inner tube is filled with a liquid for blood pressure sensing.

5. The extracorporeal life support system as claimed in claim 1, wherein the patient's heart rhythm is acquired from an electrocardiographic signal.

\* \* \* \* \*